(12) United States Patent
Hatakeyama et al.

(10) Patent No.: US 7,521,692 B2
(45) Date of Patent: Apr. 21, 2009

(54) TDI DETECTING DEVICE, A FEED-THROUGH EQUIPMENT, AN ELECTRON BEAM APPARATUS USING THESE DEVICE AND EQUIPMENT, AND A SEMICONDUCTOR DEVICE MANUFACTURING METHOD USING THE SAME ELECTRON BEAM APPARATUS

(75) Inventors: Masahiro Hatakeyama, Kanagawa (JP); Tohru Satake, Kanagawa (JP); Takeshi Murakami, Tokyo (JP); Kenji Watanabe, Kanagawa (JP); Nobuharu Noji, Kanagawa (JP)

(73) Assignee: Ebara Corporation, Tokyo (JP)

( * ) Notice: Subject to any disclaimer, the term of this patent is extended or adjusted under 35 U.S.C. 154(b) by 32 days.

(21) Appl. No.: 11/896,519

(22) Filed: Sep. 4, 2007

(65) Prior Publication Data

US 2008/0023651 A1      Jan. 31, 2008

Related U.S. Application Data

(62) Division of application No. 10/476,795, filed as application No. PCT/JP02/04655 on May 17, 2002, now Pat. No. 7,285,010.

(30) Foreign Application Priority Data

May 15, 2001     (JP)     ............................. 2001-144487
Jun. 15, 2001     (JP)     ............................. 2001-181934

(51) Int. Cl.
*G01K 1/08*     (2006.01)
*H01J 3/14*     (2006.01)
*H01J 3/26*     (2006.01)

(52) U.S. Cl. ................ 250/398; 250/492.1; 250/201.2; 250/201.3; 250/370.01; 250/310; 250/397; 250/332; 250/370.08; 439/548; 439/935; 439/559; 439/843; 439/736; 439/814; 439/81; 439/482; 348/295; 348/E5.091; 348/E5.027; 348/308; 348/164

(58) Field of Classification Search ................ 250/398, 250/492.1, 201.2, 201.3, 370.01, 310, 397, 250/332, 370.08; 439/548, 935, 559, 843, 439/736, 814, 81, 482; 348/295, E5.091, 348/E5.027, 308, 164

See application file for complete search history.

(56) References Cited

U.S. PATENT DOCUMENTS 2,138,660 A     11/1938     Mann
(Continued)

FOREIGN PATENT DOCUMENTS

EP     0 426 166     5/1991
(Continued)

OTHER PUBLICATIONS

Office Action issued Jul. 11, 2007 in Japanese Patent Office in a counterpart patent application.

*Primary Examiner*—Jack I Berman
*Assistant Examiner*—Meenakshi S Sahu
(74) *Attorney, Agent, or Firm*—Westerman, Hattori, Daniels & Adrian, LLP.

(57) ABSTRACT

An electron beam apparatus comprises a TDI sensor 64 and a feed-through device 50. The feed-through device has a socket contact 54 for interconnecting a pin 52 attached to a flanged 51 for separating different environments and the other pin 53 making a pair with the pin 52, in which the pin 52, the other pin 53 and the socket contact 54 together construct a connecting block, and the socket contact 54 has an elastic member 61. Accordingly, even if a large number of connecting blocks are provided, the connecting force may be kept to such a low level as to prevent the breakage in the sensor. The pin 53 is connected with the TDI sensor 64, in which a pixel array has been adaptively configured based on the optical characteristic of an image projecting optical system. That sensor has a number of integration stages that can reduce the field of view of the image projecting optical system to as small as possible so that a maximal acceptable distortion within the field of view may be set larger. Further, the number of integration stage may be determined such that the data rate of the TDI sensor would not be reduced but the number of pins would not be increased as much as possible. Preferably, the number of line count may be almost equal to the number of integration stages.

10 Claims, 14 Drawing Sheets

U.S. PATENT DOCUMENTS

| | | |
|---|---|---|
| 3,007,130 A | 10/1961 | Wesley |
| 3,107,966 A | 10/1963 | Bonhomme |
| 3,984,170 A | 10/1976 | Marechal |
| 4,174,145 A | 11/1979 | Berkeland et al. |
| 4,280,141 A * | 7/1981 | McCann et al. ............. 348/295 |
| 4,314,275 A | 2/1982 | Chapman |
| 4,795,977 A | 1/1989 | Frost et al. |
| 6,184,526 B1 | 2/2001 | Kohama et al. |
| 6,655,983 B1 | 12/2003 | Ishikawa et al. |
| 6,773,274 B2 | 8/2004 | Tripod |
| 6,821,145 B1 | 11/2004 | Pollock et al. |
| 7,285,010 B2 * | 10/2007 | Hatakeyama et al. ....... 439/548 |
| 2004/0173762 A1 | 9/2004 | Hatakeyama et al. |

FOREIGN PATENT DOCUMENTS

| | | |
|---|---|---|
| EP | 0 452 114 | 10/1991 |
| JP | H6-79072 | 11/1994 |
| JP | H10-197463 | 7/1998 |
| JP | 2000-149853 | 5/2000 |
| JP | 2000-251812 | 9/2000 |
| WO | WO00/73805 | 12/2000 |

* cited by examiner

_US 7,521,692 B2_

TDI DETECTING DEVICE, A FEED-THROUGH EQUIPMENT, AN ELECTRON BEAM APPARATUS USING THESE DEVICE AND EQUIPMENT, AND A SEMICONDUCTOR DEVICE MANUFACTURING METHOD USING THE SAME ELECTRON BEAM APPARATUS

CROSS-REFERENCE TO RELATED APPLICATIONS

This application is a divisional application of U.S. Ser. No. 10/476,795, now U.S. Pat. No. 7,285,010, filed Apr. 21, 2004 now U.S. Pat. No. 7,285,010, which is a national stage application of PCT/JP02/04655 filed May 14, 2002, which claims priority from Japanese application 181934/2001 filed on Jun. 15, 2001, and Japanese Application 144487/2001 filed on May 15, 2001, which are hereby incorporated by reference in their entirety. Priority under 35 USC §§120 and 121 is hereby claimed for the benefit of the filing date of U.S. patent application Ser. No. 10/476,795.

TECHNICAL FIELD OF THE INVENTION

The present invention relates to a TDI detecting device used to detect an electron image formed through a projection by an image projecting optical system, a feed-through device having a plurality of contact pins and functioning for realizing a high frequency response characteristic in such a condition having different gas pressures and/or different gas types, for example, a condition utilizing a vacuum environment and an atmospheric environment separately, and an electron beam apparatus utilizing the TDI detecting device equipped with said feed-through device, and also relates to a semiconductor device manufacturing method using said electron beam apparatus.

BACKGROUND OF THE INVENTION

FIG. 12 shows an electron beam apparatus of image projecting type according to a prior art, in which a primary electron beam is radiated onto a surface of a sample, and a secondary electron beam emitted from the surface of the sample is image-projected onto a multi-channel plate (MCP) so as to illuminate a fluorescence screen by multiplied electrons, so that a secondary electron image signal may be obtained by a plurality of detecting elements. As shown in FIG. 12, reference numeral 90 designates a TDI camera disposed in an atmospheric environment side and reference numeral 91 designates a MCP/FOP assembly disposed within a chamber in vacuum condition. This assembly 91 is equipped with a TDI (Time Delay and Integration) sensor 92, which is a suitable detecting element for the electron beam apparatus of image projecting type. The TDI sensor 92 disposed in the vacuum side is electrically connected with the TDI camera 90 disposed in the atmosphere side via a feed-through device mounted to a flange 93.

FIG. 13 and FIG. 14 show a feed-through device 94 mounted to the flange 93. As shown in FIGS. 13 and 14, the feed-through device 94 mainly comprises a plurality of pins 96 disposed in the TDI camera 90 side and attached to the flange 93, a plurality of pins 95 disposed in the TDI sensor 92 side, and a plurality of sockets 97 for connecting the pins 96 with the pins 95. Mating the pin 95 to the socket 97 as well as the pin 96 to the socket 97 may establish an electrical connection between the TDI sensor 92 disposed in the vacuum side and the TDI camera 90 disposed in the atmosphere side.

In the prior art feed-through device 94 shown in FIGS. 13 and 14, if a number of pins used for the connection is not so much, even a small connecting force (resistance force) should be sufficient for mating the pins with the sockets, but if a large number of pins is used for the connection, a great connecting force should be necessary, which sometimes causes a problem that a semiconductor sensor to be connected by the feed-through device could be broken by this great connecting force. For example, assuming that the force of 1 kg is required for the coupling of one pin and 100 pieces of pins are used for the connection, the total force of 100 kg may be required for the complete connection, which could sometimes result in a breakage of the semiconductor sensor or the like if any forced coupling would be applied.

In contrast, when a small number of pins is used for the connection, although there may occur no breakage in the semiconductor device owing to rather small connecting force, there has been another problem that, upon inspecting a wafer having an extended surface, the time required for the inspection should be longer due to such a small number of pins for connection and also a highly accurate and reliable inspection could not be carried out in an effective manner.

As for an exemplary TDI sensor 92, such a specification has been employed that includes, for example, a pixel size of 16 μm, a horizontal resolution of 2048 pixels, a number of integration stages of 512, a number of taps (a number of signal terminals of the TDI sensor) of 32, a line rate of 250 kHz, and a data rate of 25 MHz×32 (taps)=800 MHz. In this configuration, a plurality of line imaging devices, each comprising 2048 pixels of CCD imaging device arranged in a longitudinal direction, are arranged laterally in 512 lines so as to form a rectangular shape.

The TDI sensor is oriented such that the lateral direction thereof is arranged in parallel with the Y-direction corresponding to a scanning direction on a sample while the longitudinal direction thereof is arranged in parallel with the X-direction. That is, a stage transfers the sample successively along the lateral direction of the TDI sensor. At that time, a linear region on the sample covered by 2048 pixels, whose image has been picked up by one of the line imaging devices in the TDI sensor, may be subjected to the following adjacent image sensors sequentially along the scanning direction for the image thereof to be picked-up. When the stage movement is controlled to be in synchronism with the signal outputs from the line imaging device, then total 512 pieces of time delayed signals obtained through one TDI sensor by sequentially delaying the output signals from 512 pieces of line imaging devices should correspond to the image data representing the one linear region on the sample covered by the 2048 pixels. Then, the one TDI sensor adds up those 512 pieces of time delayed signals and then output the result. This adding operation can offset noise components in respective line imaging devices and thereby improve a S/N ratio of the image data signal considerably. Further, when the delay time for the output signals from the 512 line imaging devices were shifted, then similarly, total of 512 pieces of time delayed signals can be obtained also for adjacent another linear region on the sample. The one TDI sensor adds up and thus outputs those signals for each linear region in the sequential manner, and ultimately an image signal representing the entire region on the sample to be inspected can be obtained.

In the TDI sensor of the above example, an effective region will be defined as 32.768×8.192 mm, which means that when this TDI sensor is used in a defect inspection apparatus, a field of view at the image projecting position should be 33.776 mm, which is a diagonal line length of the sensor effective region. Due to this, the image projecting optical system must be designed so as to control an aberration to be below a certain value over the entire field of view at this image projecting position. The length of a lens barrel satisfying this specification could be as long as 1 m. Accordingly, a certain scale of anti-vibration system is required, which could put some restrictions on a size of the apparatus. Since a law of similitude can be applied to the optical system using exclusively an electrostatic field, if the field of view may be designed to be narrower then the length of the lens barrel can be also made shorter in proportion therewith.

In addition, if a distortion in the projected map is greater, then an image mismatch between the images at an edge area and at a central area in the integration of the TDI sensor may also become greater, and such an integrated effect may appear as an image out of focus. To handle with this problem, the design specification requires the distortion to be reduced, for example, to a degree of 1.6 μm, which is equivalent to 1/10 pixel, over the entire field of view, and this requirement leads to more complicated optical mechanism and accordingly much longer lens barrel. From the fact that the distortion is increased in proportion with a size of the field of view by cube, the smaller the field of view is, the smaller the distortion and thus the mismatch of images between the edge area and the central area in the integration will be, and also the smaller field of view allows a larger distortion and thereby the optical mechanism can be simplified and the lens barrel can be made shorter.

SUMMERY OF THE INVENTION

The present invention has been made in the light of the problems associated with the prior art as discussed above, and an object thereof is to provide a TDI detecting device with which an effect from the distortion inherent to the optics of an image projecting optical system can be eliminated as much as possible, and which at the same time enables a certain volume of data transmission to be ensured, a number of pins in a package to be optimized, a mechanism to be simplified and a length of the lens barrel to be shortened.

Another object of the present invention is to provide a feed-through device which can control a connecting force to be small even with an increased number of pins to be coupled and thereby prevent any breakage of a device such as a TDI sensor connected via the feed-through device. Still another object of the present invention is to provide a feed-through device which enables a signal transmission at high rate and high frequency, and allows an effective actuation of a number of semiconductor sensors or a CCD and/or TDI actuating at high-frequency, thereby providing an inspection for defects or the like with high reliability as well as with high throughput.

Still another object of the present invention is to provide an electron beam apparatus utilizing said TDI detecting device and said feed-through device mentioned above.

Still another object of the present invention is to provide a semiconductor device manufacturing method for improving the yield of the device products and preventing any faulty products from being delivered.

A TDI detecting device according to the present invention is characterized in having a TDI sensor for detecting an electron image formed through a projection by an image projecting optical system, in which an array of pixels in the TDI sensor is adaptively configured based on an optical characteristic of the image projecting optical system.

That is, an feature of the TDI detecting device according to the present invention resides in that by using such an extremely simple means that the array of pixels is adaptively configured based on the optical characteristic of the image projecting optical system, the effect from the distortion inherent to the optics of the image projecting optical system can be eliminated as much as possible, while enabling a certain volume of data transmission to be ensured, a mechanism to be simplified and a length of the lens barrel to be shortened.

According to a preferred embodiment of the adaptively configured array of pixels of the TDI sensor, the TDI sensor is characterized in having a number of integration stages that can reduce a field of view of the image projecting optical system to as small as possible so that a maximal acceptable distortion within the field of view may be set larger. In this embodiment, the number of integration stages may be appropriately adjusted so as to eliminate the effect of the peripheral region in the filed of view of the image projecting system, where the distortion may be magnified.

Further, preferably, the number of integration stages in the TDI sensor should be determined such that a data rate of the sensor may not be reduced but the number of pins in a package may not be increased as much as possible.

In the preferred embodiment as an example of the TDI sensor having the array of the pixels configured adaptively in the above manner, the number of lines should be almost equal to the number of integration stages.

In an alternative embodiment, above-described TDI detecting device may be provided in a state as configured into a package composed exclusively of the TDI sensors without any peripheral devices connected therewith.

In another alternative embodiment, said TDI detecting device further comprises an image processing means for processing a detection signal form said TDI sensor, a flange disposed so as to separate said TDI sensor and said image processing means into different environments respectively, and a feed-through means for operatively inter-connecting the TDI sensor and the image processing means so as to allow a signal transmission therebetween through the flange.

Preferably, said flange is used to separate the environments different in the pressure or the gas type contained therein, from each other. For example, if under a condition where the inside of the electron beam apparatus is held to be vacuum, the TDI sensor is disposed in the vacuum side while the image processing means is disposed in the atmospheric side, and the both devices are operatively interconnected by the feed-through means so as to allow the signal transmission therebetween, then the secondary electron image may be obtained appropriately under the condition where the electron beam may suffer no effect from the air.

In an especially preferred embodiment, the feed-through means comprises a second pin connected to the image processing means, which makes a pair with a first pin connected to the TDI sensor, and a socket means for connecting the first pin with the second pin, wherein the socket means is equipped with an elastic means for providing an elastic force against a connecting force between the first pin and the second pin. Preferably, a plurality of said first pins, said second pins and said sockets, respectively, is provided, so that the feed-through means may define a plurality of connecting sites.

Thus, since in the feed-through means according to the present invention, the elastic force is provided by the elastic means upon interconnecting the first pin and the second pin, the connection can be establish therebetween by only as such small connecting force as not greater than about 1/5 to 1/10 of the connecting force generated in the mating operation between the pin and the socket of the prior art.

Accordingly, since in spite of the increased number of connections, the connecting force can be reduced as a whole, the breakage of the TDI sensor upon connection can be surely prevented. Further, owing to the increased number of connections provided therein, the signal transmission at high rate and high frequency may become possible, and thereby such a TDI sensor can be realized that provides a higher data rate through a higher frequency actuation.

The TDI sensor, which has the array of the pixels configured adaptively and is connected to the image processing means via the feed-through means having the elastic means as discussed above, can be advantageously incorporated into an electron beam apparatus. An electron beam apparatus according to the present invention comprises an electron source for generating a primary electron beam, an illuminating optical system for focusing the primary electron beam into an image on a sample, an image projecting optical system for image projecting secondary electrons emitted from the sample, and a TDI detecting device as defined in the preceding discussion, which is arranged so as to detect an image-projected secondary electron image.

It should be noted that the term "secondary electron(s)" referred to in the claims and specification of this application may include a secondary electron emitted from the sample itself due to an incident energy of a primary electron and a back scattered electron resulting from a primary electron being back scattered on the sample.

In this electron beam apparatus, since the array of the pixels of the incorporated TDI sensor has been adaptively configured based on the optical characteristic of the image projecting system, the effective field of view of the image projecting optical system can be designed to be small and thereby the lens barrel in the electron beam apparatus can be made small. Further, since the acceptable distortion in the optical design can be made greater and/or the reduction in the geometric aberration other than the spherical aberration as well as the chromatic aberration other than the axial chromatic aberration can be expected, the optical mechanism can be simplified. In addition, since the TDI detecting device with an improved data rate or the like can be incorporated into the electron beam apparatus, therefore those operations, such as an evaluation of the structure on the surface of the sample, an observation through enlarged view, an evaluation of the material and an inspection for the electrical continuity, can be carried out more efficiently.

Thus, an electron beam apparatus as described above can be used to evaluate the sample or the wafer in the course of processing or after at least one of the wafer processing processes having been finished. Accordingly, so far as the surface inspection is concerned, any defects in a high-density pattern having a minimum line width equal to or less than 0.1 to 5 μm can be detected with high accuracy and high reliability as well as high throughput.

According to another aspect of the present invention, the above described feed-through means may be provided as an independent equipment. That is, this feed-through device is characterized in comprising a socket contact for interconnecting a pin connectable to one equipment and the other pin connectable to the other equipment separated by a partition means into a different environment from that of said one equipment, said socket contact having an elastic member. Further, preferably, the feed-through device may comprise a plurality of said pins, said other pins, and said socket contacts respectively so as to define a plurality of connection sites. In addition, preferably, said partition means may be used to separate the environments different in the pressure or the gas type contained therein from each other.

Said one pin of the feed-through device according to the present invention may be connected with said one equipment represented by not only the TDI but also other equipment such as a MCP, a FOP, and a CCD. Further, said other pin may be connected to the partition means.

According to still another aspect of the present invention, a socket contact for interconnecting one pin connectable to one equipment and the other pin connectable to the other equipment separated into a different environment from that of said one equipment may be provided as an independent equipment. This socket contact may be characterized in having an elastic member.

DESCRIPTION OF THE PREFERRED EMBODIMENTS

Preferred embodiments of the present invention will now be described with reference to the attached drawings.

(TDI Sensor)

An embodiment for determining an optimized number of integration stages of a TDI sensor will be discussed below. Table 1 indicates a field of view, that is, a diagonal line length of a sensor effective region, and a maximal acceptable distortion across an entire field of view of a TDI sensor for different horizontal resolutions and different numbers of integration stages with a total number of the pixels thereof remained almost equal to that of an existing TDI sensor.

TABLE 1

| Horizontal resolution | Number of integration stage | Field of view μm | Maximal acceptable distortion δmax μm |
|---|---|---|---|
| 2048 | 512 | 33757 | 1.54 |
| 1024 | 1024 | 23148 | 2.22 |
| 768 | 1366 | 25052 | 3.22 |
| 512 | 2048 | 33757 | 4.76 |

It can be seen from the Table 1 that the field of view is minimized for the TDI sensor with the number of integration stages of 1024 and the maximal acceptable distortion becomes greater as the number of integration stages becomes greater.

Figure 1:
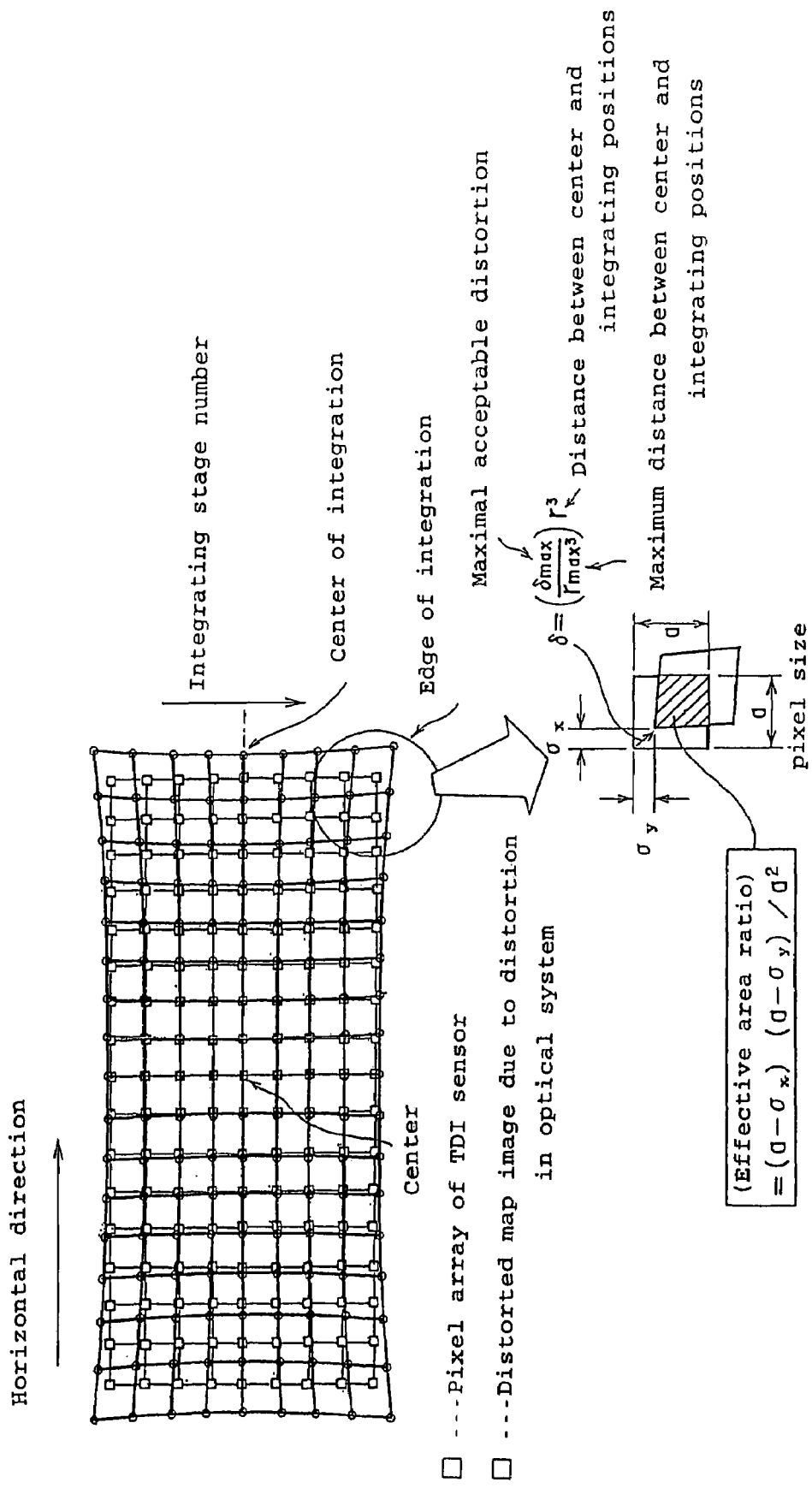
FIG. 1 is a schematic diagram for illustrating an adaptive configuration of a pixel array in a TDI sensor according to the present invention.

FIG. 1 illustrates how to determine the maximal acceptable distortion. A lattice depicted by a thin line indicates a pixel array of the TDI sensor. An image projected on an acceptance plane of the TDI sensor by an image projecting optical system should appear to be an image corresponding to the pixel array of the TDI sensor if there is no distortion, but the map may be projected to be such a lattice as depicted by a thick line because there is a distortion. Since a magnitude of the distortion is in proportion to the distance from the center of the field of view by cube, therefore a greater distortion may be observed in the peripheral portion of the image rather than in the central portion thereof, with the maximal distortion induced at a corner of the image. Accordingly, assuming that the maximal acceptable distortion is denoted as $\sigma_{max}$ and the distance between the center of the image and the corner of the image is denoted as $r_{max}$, the distortion $\delta$ measured at a location having a distance r from the center of the image may be expressed by an equation: $\delta = (\sigma_{max}/r_{max})r^3$.

If such a distorted image is projected on the acceptance plane of the TDI sensor, some of the image data, which otherwise should be entered into the pixels of the TDI sensor, may fall out of the range. When such images are accumulated by the number of integration stages in the integrating direction, it may lead to a deteriorated contrast or an unfocused image in its line pixel. To determine this magnitude quantitatively, an effective area ratio is introduced into the evaluation. The effective area ratio is defined as an overlapped area of each pixel of the TDI sensor with the image data projected with some offset due to the distortion (the area defined by the hatching) divided by a pixel area. Although, in practice, the image data projected with offset may also appear to be distorted in its shape, this effect should not be taken into account in this approach but the position mismatch is exclusively considered. Since the magnitude of the position mismatch is represented by the $\delta$ as described above, and the direction of position mismatch is determined as a direction defined by a line connecting the center of the image and the position of the pixel in concern, therefore assuming that the horizontal distance from the center of the image to the pixel position is denoted as $r_x$, the distance along the direction of the integration stages is denoted as $r_y$, the horizontal component of the position mismatch is denoted as $\sigma_x$, and the component of the position mismatch along the direction of the integration stages is denoted as $\sigma_y$, then the following relations may be established:

$$\sigma_x = \delta r_x/r, \; \sigma_y = \delta r_y/r.$$

Accordingly, the effective area ratio Rs is expressed by the equation:

$$Rs = (a - \sigma_x)(a - \sigma_y)/a^2$$

$$= (a - (\delta_{max}/r_{max}^3)r^3 r_x/r) \times (a - (\delta_{max}/r_{max}^3)r^3 r_y/r)/a^2,$$

where "a" is a pixel size.

A level of contrast or defocus of the image in the line pixel may be evaluated based on a value of $\Sigma Rs/n$, which is defined as a value of the integration of the effective area ratio in each pixel, Rs, divided by the number of integration stages in the integrating direction, n, so as to be averaged.

In this approach, the values in the above-described Table 1 are used to determine the $\delta_{max}$ which satisfies the expression of $\Sigma Rs/n = 0.9$ (i.e., the averaged area mismatch of 10%). In the above process, the pixel array of the TDI sensor has been optimized with the optical characteristic taken into consideration, and further, it is preferable that even after the optimization, the inspection throughput may be ensured as high as the existing one. To achieve this, the data transmission volume per unit hour should be set equally.

The existing TDI sensor is able to transmit 2048 pieces of image signals during a time period of 1/250 kHz=4 μs. However, the data rate for properly taking out the signals from one signal terminal without suffering from any noise is currently in the range of 25 MHz. Based on this fact, in the current practice, the 2048 pieces of image signals are transmitted by a partial charge of each of 32 signal terminals. That is, it is sufficient to take out 2048/32=64 pieces of image signals from each one of the signal terminals during 4 μs. From 4 μs×25 MHz=100, it is apparent that 64 pieces of image signals can be surely taken out. In practice, it is required to ensure an extra time, in addition to that for 64 pieces of image signals, for the overclocked pixel count of around 20 as converted into the data rate, in order to transfer the charges accumulated in the integrating direction to the CCD for the data transmission. Accordingly, 64+20=84<100, indicating the data rate above is still considered sufficient.

As discussed above, the TDI sensor having the optimized pixel array tends to have a greater number of integration stages, while inversely the number of pixels in the horizontal direction is apt to be decreased. Accordingly, the number of image signals which can be transmitted in one cycle of the line rate is decreased. That is, if it is not desired that the image signal transmission volume per unit time would be reduced, the line rate must be increased. Since the upper limit of the data rate representing a transmission capacity at one signal terminal is unchangeable, the data volume obtainable from the one signal terminal in one cycle of the line rate would be decreased. Total volume of image signals to be transmitted during a cycle of the line rate would also be decreased, but in order to compensate for the reduced data transmission volume per signal terminal, the number of the signal terminals should be increased, which leads to the increase in number of pins in the TDI sensor and/or the extension in package area.

Table 2 shows a required line rate, a limit data transmission volume, a number of signal terminals and a data transmission volume per cycle per signal terminal in the TDI sensor having different pixel arrays. The limit data transmission volume is determined from 25 MHz divided by the line rate, and the data transmission volume per cycle per signal terminal is determined from the horizontal resolution divided by the number of signal terminals and then further added with the number of overclocked pixels=20. The number of signal terminals has been determined so that the data transmission volume per cycle per signal terminal could not exceed the limit data transmission volume. From the Table 2, it can be seen that when the horizontal resolution has fallen down to be less than 1024, the number of signal terminals increases rapidly. The number of pins installed in the existing TDI sensor is about 200. It is not exactly the fact that the number of the pins should be increased simply in proportion to the number of the signal terminals, but if so assumed, the TDI sensor requires the number of pins to be 500 for the horizontal resolution of 768 and the number of pins to be 1000 for the horizontal resolution of 512. Such increase in the number of pins is not preferred because especially in the case of the TDI sensor used in the vacuum atmosphere within a lens barrel, the cost for the feed-through device used to take out the signal to the atmospheric environment may be increased extremely.

TABLE 2

| Horizontal resolution | Number of integration stage | Line rate Hz | Limit data transmission volume | Data transmission volume per cycle | Number of signal terminal |
|---|---|---|---|---|---|
| 2048 | 512 | 2.5E+05 | 100 | 84 | 32 |
| 1024 | 1024 | 5.0E+05 | 50 | 46 | 40 |
| 768 | 1366 | 6.7E+05 | 37 | 30 | 80 |
| 512 | 2048 | 1.0E+06 | 25 | 23 | 160 |

It has been found from the result of examination for optimizing the pixel array in the TDI sensor in consideration of the optical characteristic and the number of signal terminals thereof, that the TDI sensor with the pixel array defined as the horizontal resolution of 1024× the number of integration stages of 1024 is optimal as a detecting device in an electron beam defect inspection apparatus using the image projecting optical system, because of the smallest field of view and the lower increase in the number of signal terminals.

Further, it is expected that since this TDI sensor has the field of view ⅔ times as large as that of the existing one, the lens barrel may be possibly reduced in size approximately by ⅔ times as compares with the existing one according to the law of similitude. In addition, it is also expected, in association with the reduced field of view, that the geometric aberration other than the spherical aberration and the chromatic aberration other than the axial chromatic aberration could be reduced.

(Feed-through Equipment)

Figure 2:
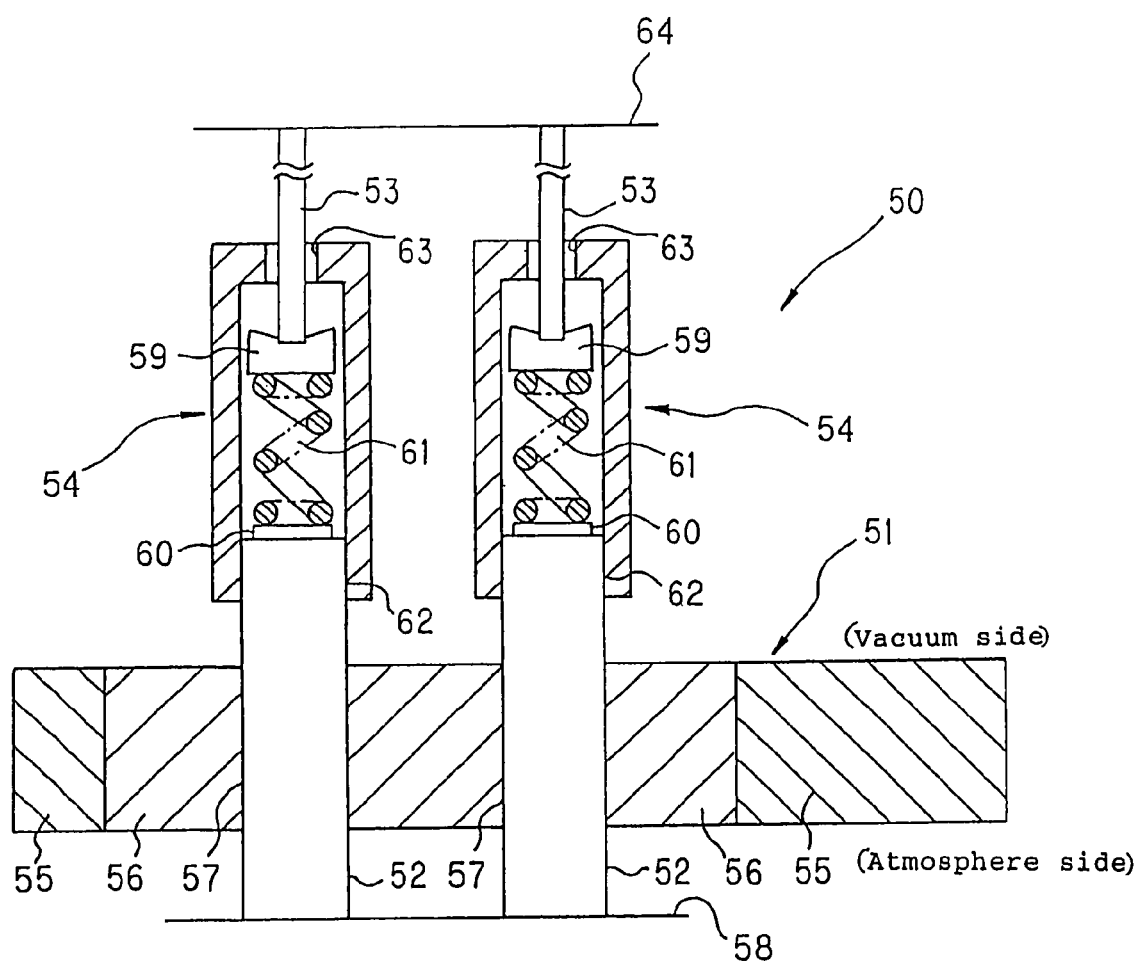
FIG. 2 is a sectional view showing an embodiment of a field-though device according to the present invention.

Preferred embodiments of a feed-through device according to the present invention will now be described with reference to the attached drawings. Referring to FIG. 2, reference numeral 50 generally designates a feed-through device. This feed-through device 50 comprises as main components a socket contact 54 for interconnecting one pin 52 mounted to a flange 51 for separating different environments and the other pin 53 making a pair with said one pin 52. The illustrated flange 51 separates an atmospheric environment (the lower region defined in FIG. 2) and a vacuum environment (the upper region defined in FIG. 2).

The flange 51 comprises an outer piece 55 made of metal flange and an inner piece 54 made of insulating material such as glass or ceramic. The inner piece 56 is attached to the outer piece 55 by welding process or the like so as to be formed into a single body. One or more through-holes 57 are formed in the inner piece 56, through which the pin 52 is secured fixedly by silver-alloy brazing or the like. Metal, such as Kovar, having a thermal expansion coefficient nearly equal to that of said insulating material may be used as a material for making the pin 52. A bottom end of the pin 52 is connected to a device 58, such as a TDI camera, disposed in the atmosphere side. On the other hand, a top end of the pin 52 is fitted in a coupling hole 62 in the bottom end side of the socket contact 54.

In the socket contact 54, a coil spring 61 or an elastic member with seats 59 and 60 attached to respective ends thereof is operatively arranged so as to be movable in an axial direction of the socket contact 54 (up-and-down direction in the drawing). The seat 60 disposed in the bottom end side of the coil spring 61 is adapted to come into contact with the top end of the pin 52.

A coupling hole 63 having a bore diameter smaller than that of the coupling hole 62 disposed in the bottom end side is formed in the top end side of the socket contact 54, through which the other pin 53 making the pair with the pin 52 is inserted. Metal, such as Kovar, having a thermal expansion coefficient nearly equal to that of said insulating material may be used as a material for making the pin 53. As illustrated, the bottom end of the pin 53 is adapted to come into contact with the seat 59 disposed in the top end side of the coil spring 61. Besides, the top end of the pin 53 is connected to a device 64, such as a TDI sensor, disposed in the vacuum side. Although the device 64 is preferably a TDI sensor equipped with the pixel array shown in FIG. 1 having been configured adaptively, the device 64 may be any other semiconductor devices.

With a configuration in which the pin 62 comes into contact with the seat 60 and the pin 53 comes into contact with the seat 59, an electrical connection may be established between the device 58, such as the TDI camera, disposed in the atmosphere side and the device 64, such as the TDI sensor, disposed in the vacuum side. Further, the pin 52, the pin 53 and the socket contact 54 having the coil spring 61 with the seats 59, 60 attached to respective ends thereof, together construct a connecting block of the feed-through device 50, and a plurality of connecting blocks may be arranged in the equipment. FIG. 2 shows the feed-through device 50 with two connecting blocks arranged therein.

Figure 6:
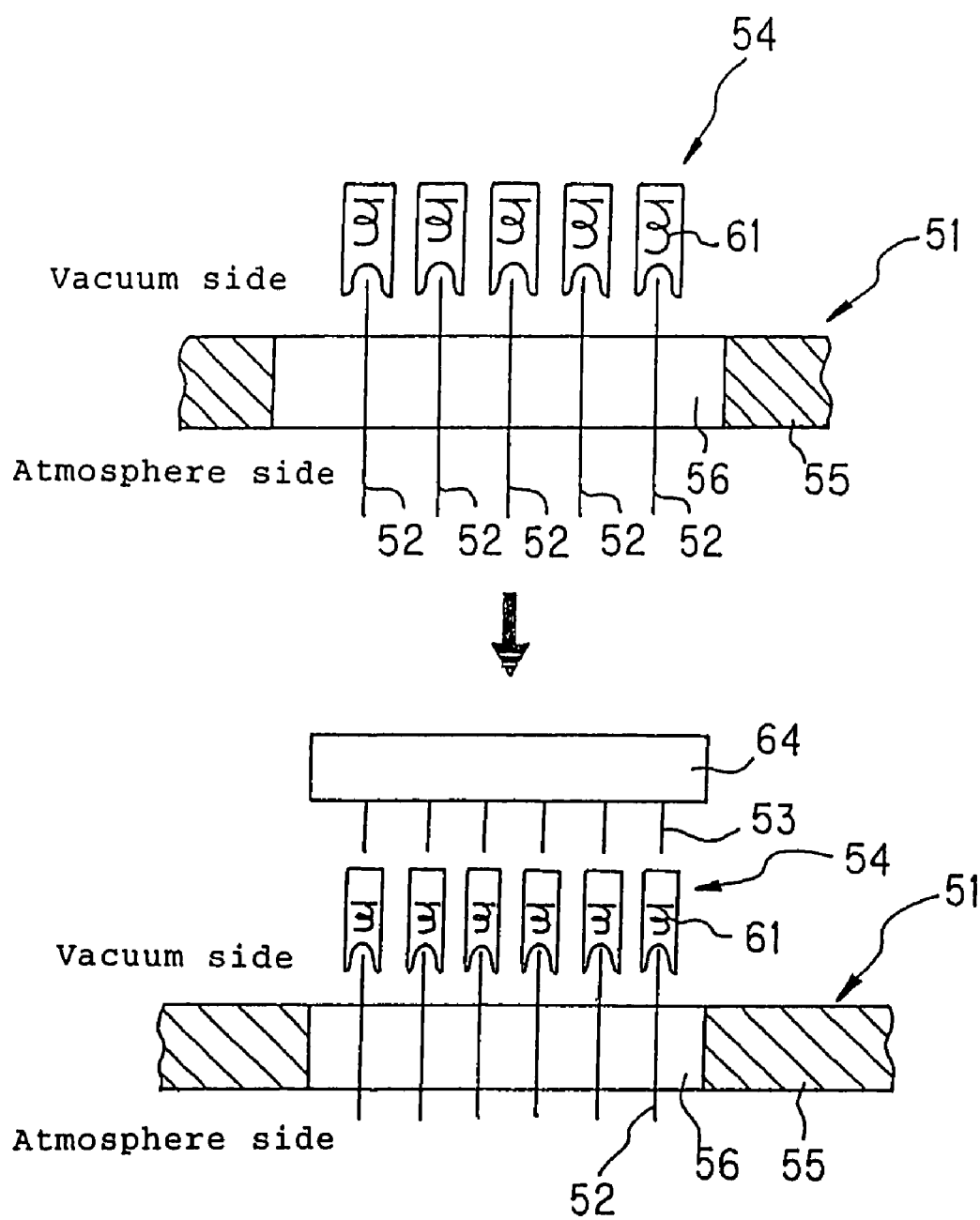
FIG. 6 is a schematic sectional view illustrating a mounting procedure of a connecting block applicable to said embodiment.

Now, a coupling procedure for the connecting block of the feed-through device 50 will be described. As shown in FIG. 2 and FIG. 6, the top end portion of the pin 52 secured fixedly to the flange 51 is fitted in the coupling hole 62 in the bottom end side of the socket contact 54. This fitting brings the top end of the pin 52 into contact with the seat 60 disposed in the bottom end side of the coil spring 61 within the socket contact 54. Subsequently, the bottom end portion of the pin 53 is inserted into the coupling hole 63 in the upper end side of the socket contact 54, so as to be compressed against the seat 59 disposed in the top end side of the coil spring 61. The coil spring 61 is brought into a contracted state in the axial direction of the socket contact 54 (the up-and-down direction in FIG. 2), so that the coil spring 61 pushes (biases) the pin 52 and the pin 53 outwardly along said axial direction via the seats 59, 60.

This may cause the pin 52 and the pin 53 to be electrically interconnected via the coil spring 61 including the seats 59 and 60 attached to respective ends thereof, and thus the device 58, such as the TDI camera, disposed in the atmosphere side and the device 64, such as the TDI sensor, disposed in the vacuum side are electrically interconnected.

Figure 5:
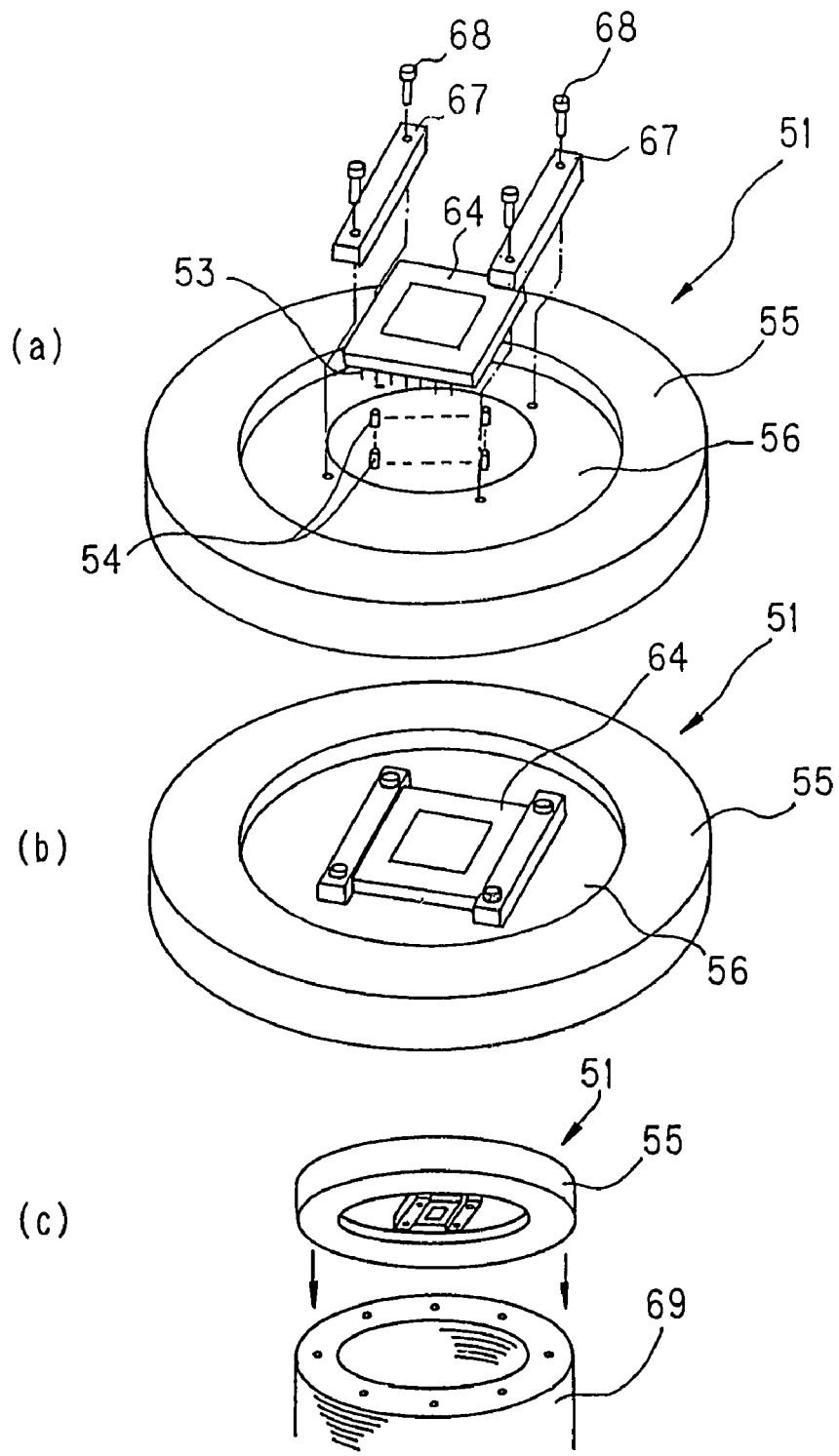
FIG. 5 is a schematic perspective view illustrating a procedure for installing a device, which is applicable to said embodiment and is disposed in the vacuum side, in a chamber of a surface inspection apparatus.

Further, FIG. 5 shows an installation procedure for the case where the device 64, such as the TDI sensor, disposed in the vacuum side is to be installed in a chamber of a surface inspection apparatus. At first, as discussed above, the top end portion of the pin 52 secured fixedly to the inner piece 56 of the flange 51 is fitted in the coupling hole 62 in the bottom end side of the socket contact 54. This fitting brings the top end of the pin 52 into contact with the seat 60 disposed in the bottom end side of the coil spring 61 within the socket contact 54.

Then, as shown in FIG. 5(a), the bottom end portion of each of the plurality of pins 53 connected to the device 64, such as the TDI sensor, is inserted into the coupling hole 63 in the top end side of each of the socket contacts 54, and thus pressed against the seat 59 disposed in the top end side of the coil sparing 61 as shown in FIG. 2. The coil spring 61 is brought into a contracted state in the axial direction of the socket contact 54 (in the up-and-down direction in FIG. 2), so as to push (force) the pin 52 and the pin 53 outwardly along said axial direction via the seats 59 and 60. This may cause the pin 52 and the pin 53 to be electrically interconnected via the coil spring 61 with the seats 59 and 60 attached to respective ends thereof, and thus the device 58, such as the TDI camera, disposed in the atmosphere side and the device 64, such as the TDI sensor, disposed in the vacuum side are electrically interconnected.

Further, as the bottom end portion of each of the plurality of pins 53 connected to the device 64 such as the TDI sensor is inserted into the coupling hole 63 disposed in the top end side of each of the socket contacts 54, then, as shown in FIG. 5(b), the device 64 such as the TDI sensor is successively mounted on the socket contact 54. An outer frame of the device 64 is provided with a retaining member 67, which will be secured to the inner piece 56 of the flange 51 by using a screw 68, thereby ensuring the device 64 to be rigidly mounted on the flange 51. The flange 51 with the device 64 mounted thereon is in turn mounted onto the chamber 69, as shown in FIG. 5(c), such that the side on which the device 64 is mounted is oriented toward the vacuum side.

According to the above embodiment, since the connection between the pin 53 and the socket contact 54 and thus the pin 52 is established by inserting the pin 53 connected to the device 64 such as the TDI sensor into the coupling hole 63 of the socket contact 54 so as to be compressed against the seat 59 in opposition to the pushing force (bias force) of the coil spring 61, therefore this connection only requires such a connecting force as small as not greater than about ⅕ to 1/10 of the connecting force applied to the mating of the pin with the socket in the prior art.

For example, if the semiconductor sensor including the TDI is employed as the device 64 disposed in the vacuum side and said sensor is provided with 200 pieces of pins for a data transmission rate as high as 500 MHz or higher, the connecting force of approximately 200 kg has been necessary in the prior art and therefore such a device as TDI could have been broken sometimes due to the forced connection, but in contrast, according to the above embodiment, the connection can be easily established with an extremely small connecting force and accordingly possible breakage as above can be prevented.

Because of the small connecting force, the present feedthrough connecting system is quite effective especially in the case of a large number of pins, i.e., a large number of said connecting blocks being arranged. Further, providing the large number of said contact blocks enables the signal transmission at higher rate and higher frequency so as to realize an effective actuation of a number of semiconductor sensors or CCD and/or TDI actuating at high frequency, thereby allowing those operations, such as an evaluation of the structure on the surface of the sample, an observation through enlarged view, an evaluation of the material and an inspection for the electrical continuity to be carried out more efficiently. Yet further, so far as the inspection on the surface is concerned, any defects in the high-density pattern having a minimum line width equal to or less than 0.1 to 5 μm can be detected with high accuracy and high reliability as well with high throughput.

Although in the above embodiment, the flange 51 is used to separate the atmospheric environment (the lower region in FIG. 2) and the vacuum environment (the upper region in FIG. 2) from each other, the present invention is not limited to this configuration but the flange 51 may be used to separate any environments having different pressures or containing different gas types. Further, although with respect to the flange 51, the device 58 has been arranged as the device disposed in the atmosphere side thereof and the TDI is arranged as the device 64 disposed in the vacuum side thereof, the present invention is not limited to this but such a device as MCP, FOP, or CCD may be connected to the flange 51.

Figure 3:
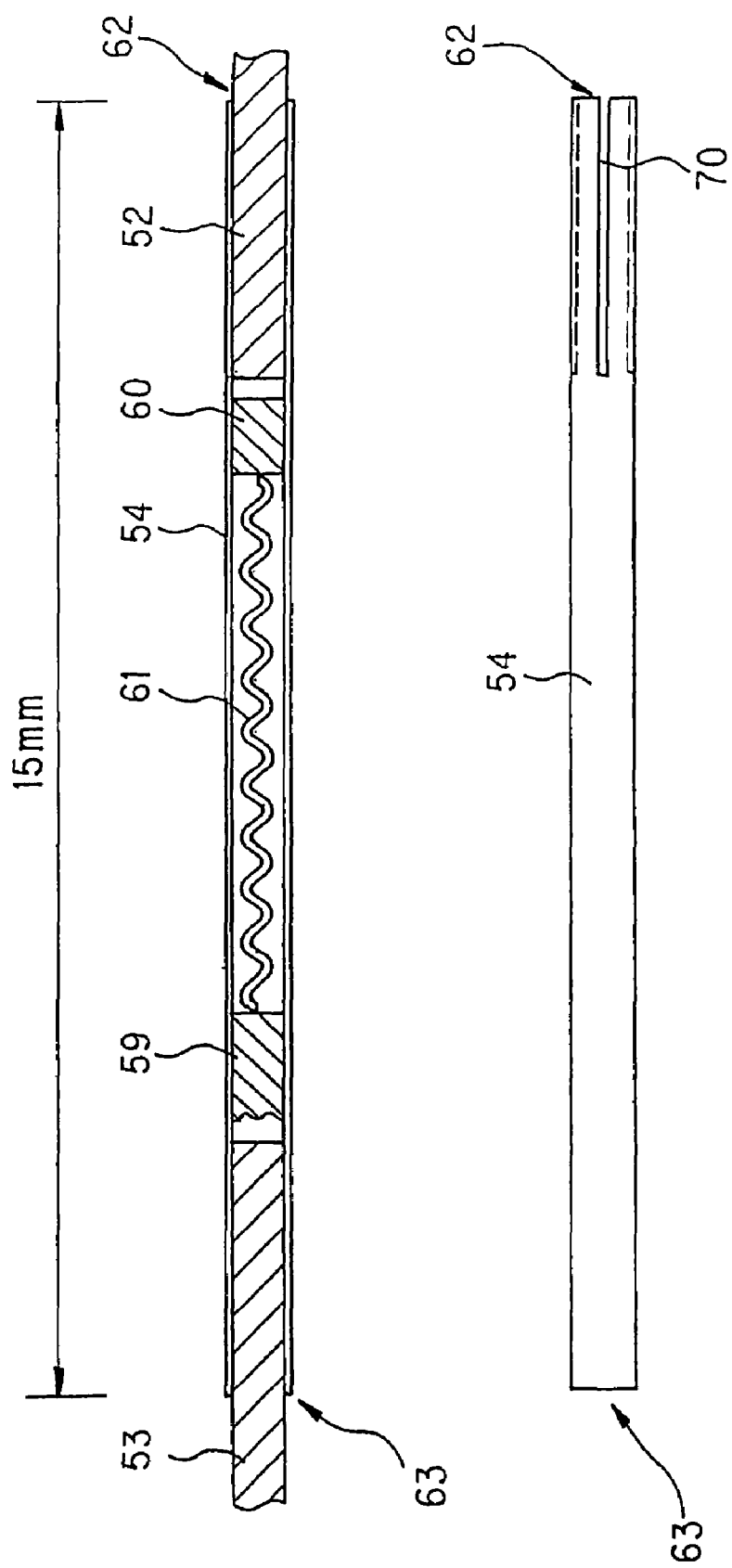
FIG. 3 shows a sectional view and a side view of an example of a socket contact applicable to the feed-through device according to the present invention.

Alternatively, as shown in FIG. 3, the socket contact 54 may be designed such that an inner diameter is 0.5 mm, a wall thickness is 0.2 mm and a length is 15 mm, and further a slit 70 is formed in one end where the pin 52 is to be inserted, i.e., a coupling hole 62 is formed, so as to extend along the axial direction of the socket contact 54. Providing such a slit 70 may facilitate the fitting of the pin 52 into the coupling hole 62 of the socket contact 54.

Figure 4:
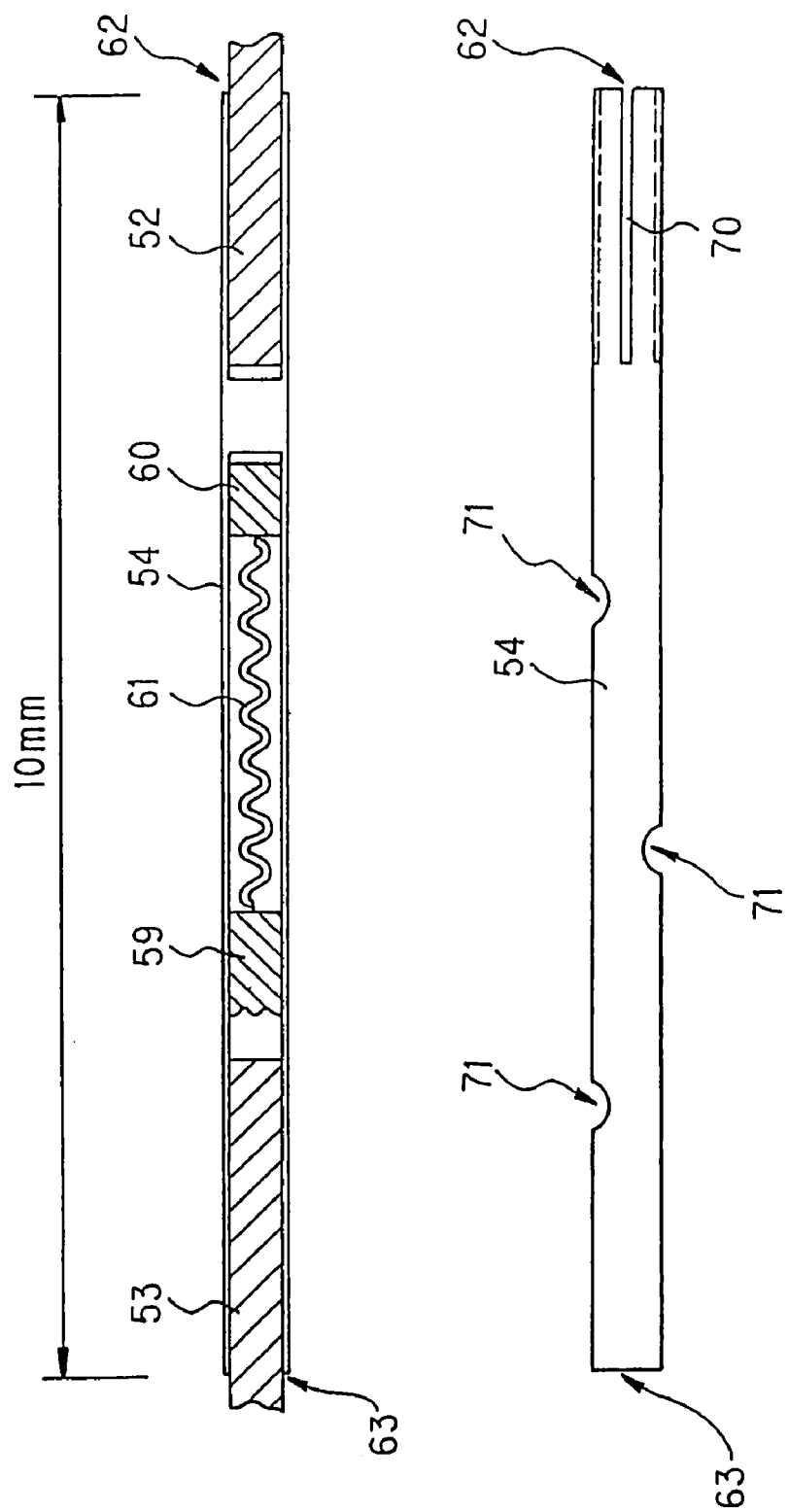
FIG. 4 shows a sectional view and a side view of another example of a socket contact applicable to the feed-through device according to the present invention.

Further, if the socket contact 54 is to be placed in an environment of different pressure, such as a vacuum environment, one or more vent holes 71 may be formed in a side face of the socket contact 54, as indicated by reference numeral 71 in FIG. 4, so that the vacuum evacuation may be applied to the inside of the socket contact 54 via this vent holes 71, thus to prevent the deterioration of the gas pressure in the surroundings. In this regard, if no vent hole 71 is provided, the gas in the socket contact 54 may be discharged little by little from the coupling holes 62, 63 disposed in the opposite ends of the socket contact 54, which may have such a negative effect as placing a limitation on the surrounding vacuum pressure. In addition, if such a sensor as a MCP or a CCD sensible to the pressure environment is used, sometimes the operating lifetime of the sensor could be deteriorated.

Figure 7:
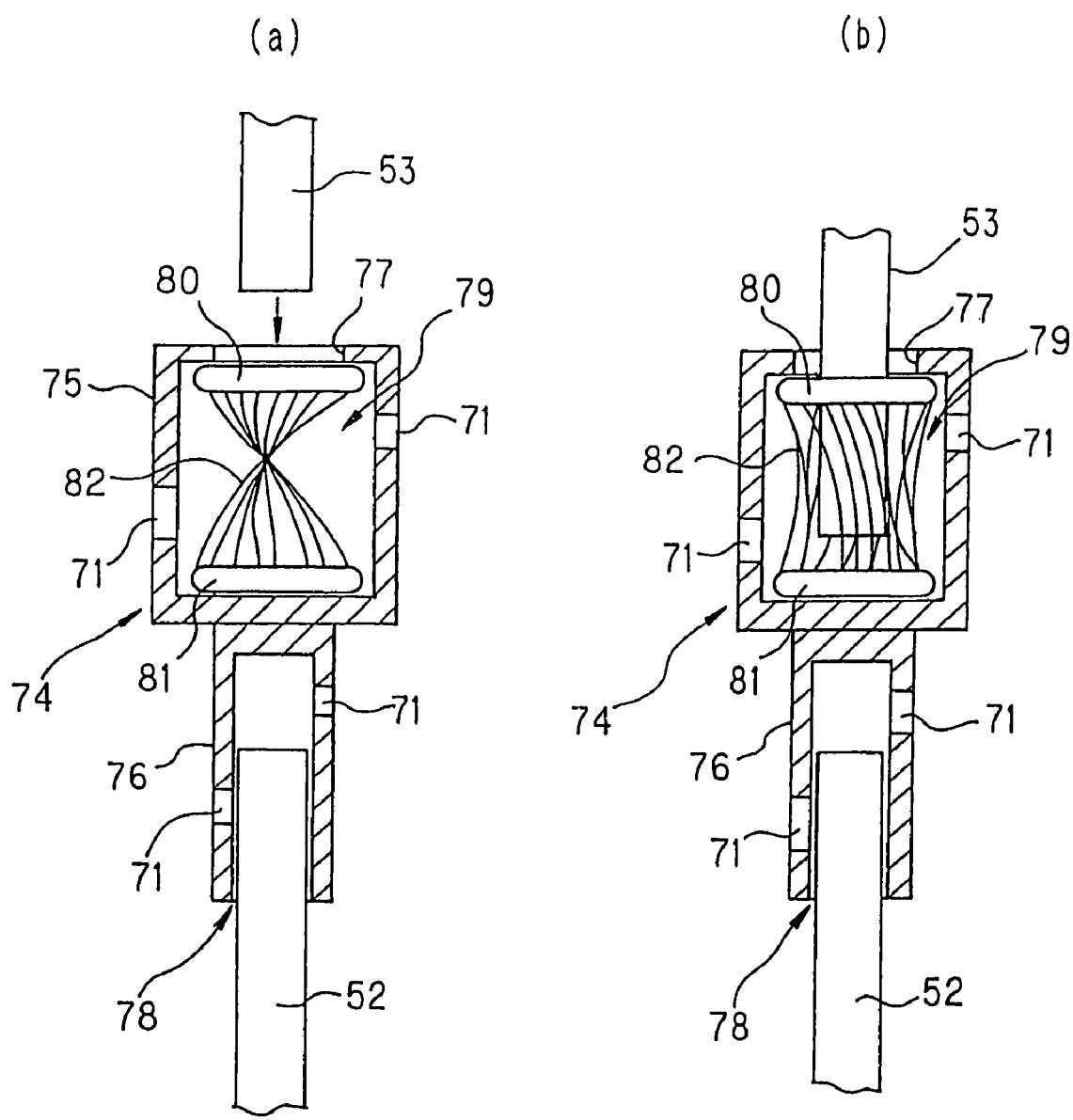
FIG. 7 is a partial sectional view of still another example of a socket contact applicable to the feed-through device according to the present invention.

In the embodiments described above, the coil spring has been employed as the elastic member, but other element such as a spiral band may be used as the elastic member. FIG. 7 shows an example in which a spiral band is used as the elastic member. As shown in FIG. 7(a), the socket contact 74 is made up of an integral unit consisting of an upper socket 75 and a lower socket 76. A coupling hole 77, into which the pin 53 is to be inserted, is formed in a top end of the upper socket 75, and the vent hole 71 is formed in a side surface thereof. Similarly, a coupling hole 78, into which the pin 52 is to be fitted, is formed in a bottom end of the lower socket 76, and the vent hole 71 is formed in a side surface thereof. The bottom end of the upper socket 75 is rigidly attached to the top end of the lower socket, thus to make up the socket contact 74.

Within the upper socket 75, the spiral band 79 is provided as the elastic member. The spiral band 79 comprises an upper ring 80, a lower ring 81 and a bundle of elastic spiral wires 82. The spiral wire bundle 82 functions for connecting the upper ring 80 with the lower ring 81. Each of the wire components of the spiral wire bundle 82 is extending spirally between the upper ring 80 and the lower ring 81. This spiral band 79 is accommodated within the upper socket 75 with the lower ring 81 attached to the inner bottom surface of the bottom end of the upper socket 75. The upper ring 80 has been configured so as for the inner diameter thereof to be greater than the outer diameter of the pin 53.

A coupling procedure will now be described. At first, the upper end portion of the pin 52 is inserted into the coupling hole 78 of the lower socket 76. Then, the bottom end portion of the pin 53 is inserted through the coupling hole 77 of the upper socket 75, advanced through the upper ring 80 of the spiral band 79, and then pushed into the spiral wire bundle 82 against an inward elastic force exerted thereby. As the pin 53 has been inserted through the upper ring 80 and pushed into the spiral wire bundle 82, then, as shown in FIG. 7(b), the upper ring 80 is revolved relative to the lower ring 81, so that the spiral wire bundle 82 is brought into such a condition where the central portion of the bundle 82 has been pressed to expand outwardly. In this condition, the spiral wire bundle 82 exerts its own elastic force around the pin 53 to press the pin 53 inwardly. This can establish an electrical connection between the pin 52 and pin 53 through the spiral band 79, the upper socket 75 and the lower socket 76. As discussed above, since as the pin 53 is inserted into the upper socket 75 in its central portion, one ring is revolved with respect to the other ring, thus to accommodate the insertion, therefore the resistance upon insertion may be reduced and the coupling operation may be carried out more easily.

As explained above, since in the above embodiment, the electrical connection between the pin 53 and the socket contact 74 and thus the pin 52 is established by pushing the pin 53 into the spiral wire bundle 82 against the inward elastic force of the spiral wire bundle 82, therefore this connection only requires such a connecting force as small as not greater than about ⅕ to 1/10 of the connecting force applied to the mating of the pin with the socket in the prior art. In addition, since the connection has been established under a condition of the wires winding around the pin, the impedance in the connection may be reduce and thereby a high frequency (e.g., 150 MHz or higher) response of the signal can be accomplished.

Since the connecting force of this spiral band type is as small as that of the embodiment shown in FIGS. 2, 5 and 6, this connecting system is quite effective especially in the case of a large number of pins as many as, for example, 100 or more, i.e., a large number of said connecting blocks being arranged. Further, providing the large number of said contact blocks enables the signal transmission at higher rate and higher frequency so as to realize an effective actuation of a number of semiconductor sensors or CCD and/or TDI actuating at high frequency, thereby allowing those operations, such as an evaluation of the structure on the surface of the sample, an observation through enlarged view, an evaluation of the material and an inspection for the electrical continuity to be carried out more efficiently. Yet further, so far as the inspection on the surface is concerned, any defects in the high-density pattern having a minimum line width equal to or less than 0.1 to 5 μm can be detected with high accuracy and high reliability as well with high throughput.

Figure 8:
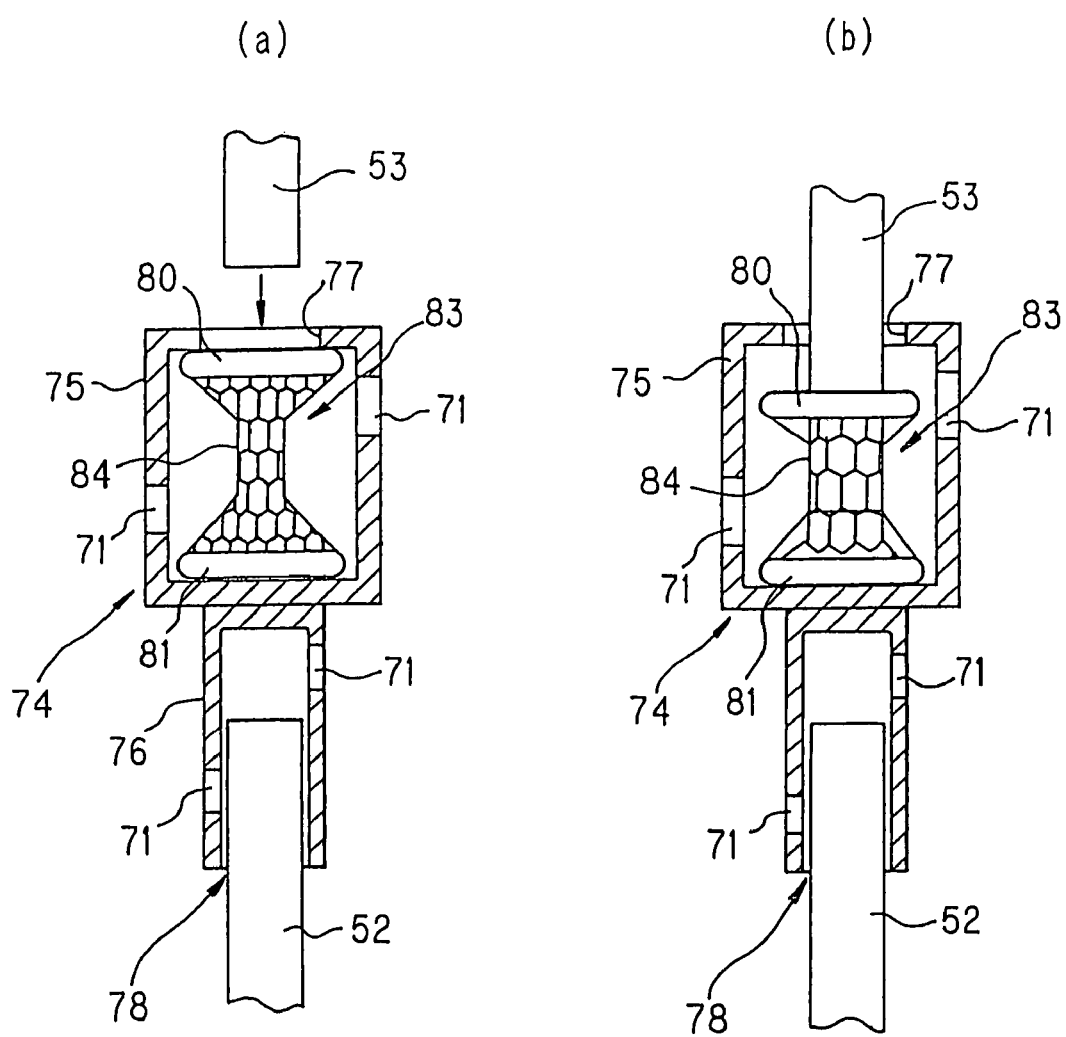
FIG. 8 is a partial sectional view of still another example of a socket contact applicable to the feed-through device according to the present invention.

In the embodiment shown in FIG. 7, the spiral band 79 is used as the elastic member, and alternatively, instead of the spiral band 79, a net band 83 may also be used as the elastic member, as shown in FIG. 8. The net band 83 comprises an upper ring 80, a lower ring 81 and an elastic net 84. The net 84 functions for connecting the upper ring 80 with the lower ring 81. In a coupling procedure, at first, the top end portion of the pin 52 is fitted in the coupling hole 78 of the lower socket 76, as shown in FIG. 8(a). Then, the bottom end portion of the pin 53 is inserted through the coupling hole 77 of the upper socket 75, advanced through the upper ring 80 of the net band 83, and pushed into the net 84 against the inward elastic force exerted thereby. When the pin 53 has been inserted through the upper ring 80 and pushed into the net 84, the net 84 is brought into a condition where the central portion thereof is pushed to expand outwardly, while the upper ring 80 is moving toward the lower ring 81, as shown in FIG. 8(b). In this condition, the net 84 exerts its own elastic force around the pin 53 to push the pin inwardly. This may establish an electrical connection between the pin 52 and the pin 53 through the net band 83, the upper socket 75 and the lower socket 76. As discussed above, since when the pin 53 is inserted into the central portion of the upper socket 75, one ring is moved in the direction to come closer to the other ring and thereby accommodate this insertion, therefore the resistance upon insertion may be reduced and the coupling may be carried out more easily. Alternatively, different from the above embodiment, a plurality of diagonally tied wires may be used, rather than the spiral wires. In this case, when the pin inserted, the wires adjacent to the inserted portion may wind around the pin and is expanded accordingly. By this way, the number of contacts with the pin may be increased, thus to improve the high frequency characteristic of the signal and the transmission characteristic of the high current at contacts.

As described above, since the electrical connection is established between the pin 53 and the socket contact 74 and thus the pin 52 by pushing the pin 53 into the net 84 against the inward elastic force of the net 84, therefore this connection only requires such a connecting force as small as not greater than about ⅕ to 1/10 of the connecting force applied to the mating of the pin with the socket in the prior art. In addition, since the impedance in the connection may be reduce, a high frequency (e.g., 150 MHz or higher) response of the signal can be accomplished.

Since the connecting force of this net band type is as small as those of the embodiments shown in FIGS. 2, 5, 6 and/or 7, this connecting system is quite effective especially in the case of a large number of pins as many as, for example, 100 or more, i.e., a large number of said connecting blocks being arranged. Further, providing the large number of said contact blocks enables the signal transmission at higher rate and higher frequency so as to realize an effective actuation of a number of semiconductor sensors or CCD and/or TDI actuating at high frequency, thereby allowing those operations, such as an evaluation of the structure on the surface of the sample, an observation through enlarged view, an evaluation of the material and an inspection for the electrical continuity to be carried out more efficiently. Yet further, so far as the inspection on the surface is concerned, any defects in the high-density pattern having a minimum line width equal to or less than 0.1 to 5 μm can be detected with high accuracy and high reliability as well with high throughput.

(Electron Beam Apparatus)

An electron beam apparatus of image projecting type using the feed-through device described above will now be described. It is to be noted that a sensor, such as a TDI sensor having been described with reference to FIG. 1, a EBCCD, a CCD, which detects electrons and outputs a signal, or another sensor which detects light and outputs a signal may be used as the device to be disposed in the vacuum side (the device designated by reference numeral 64 in FIG. 2). In addition, an object to be inspected may be a silicon wafer and a pattern structure in the course of the process for manufacturing a semiconductor circuit on the surface of the wafer. It is also to be understood that a beam such as an electron beam is radiated for carrying out an inspection in order to determine whether or not there is a defect, such as dust, a bad continuity, a bat pattern, or lack, to determine a condition, or to determine a type for sorting.

Figure 9:
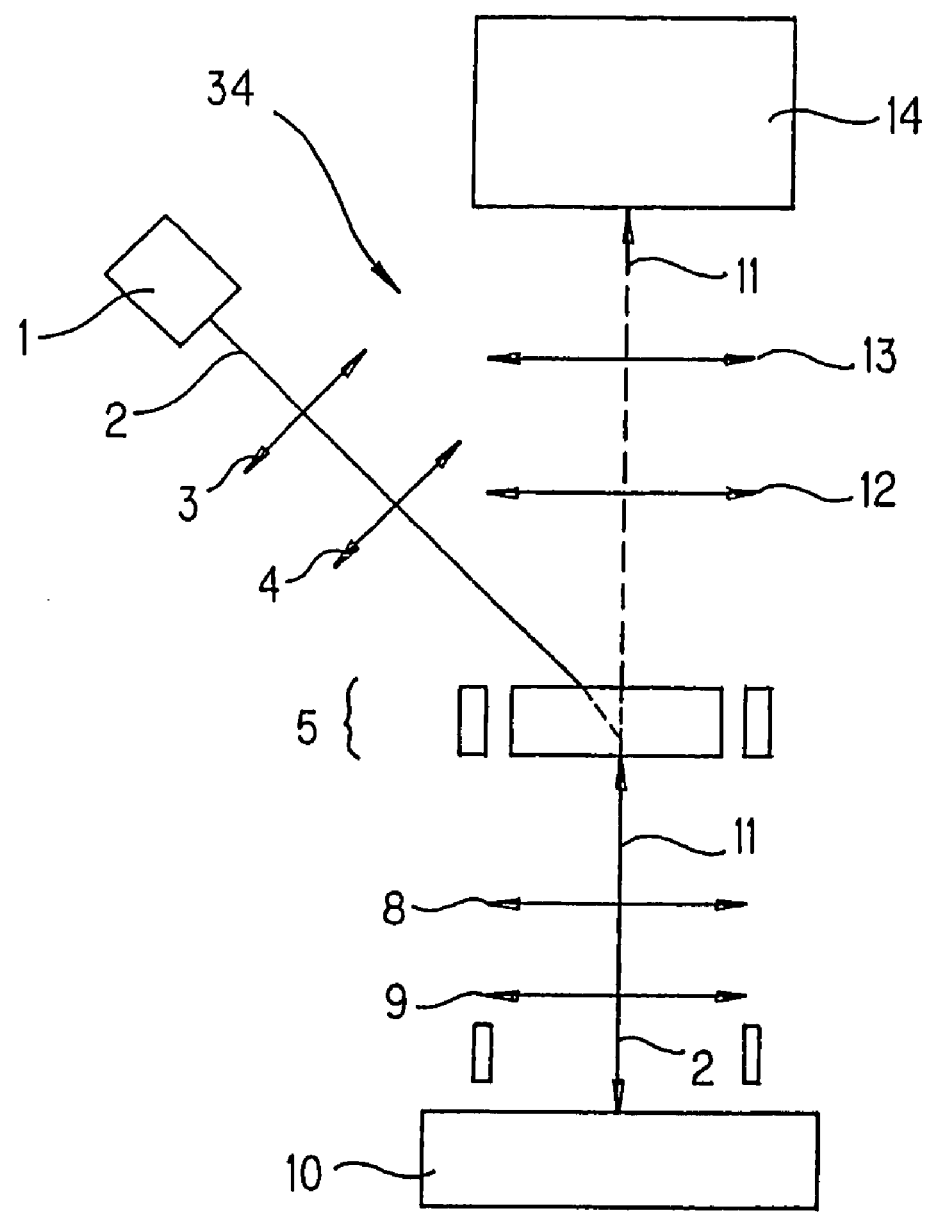
FIG. 9 is a schematic diagram of an electron beam inspection apparatus of an image projecting type using the feed-through device according to the present invention.

As shown in FIG. 9, an electron beam 2 emitted from an electron gun 1 is formed into a rectangular shape by a shaping aperture (not shown), and contracted by two-stage of reducing lenses 3, 4 so as to be properly shaped and thus to be focused into an image of 1.25 mm square in a deflection center surface of an E×B filter 5. The adequately shaped beam is deflected by the E×B filter 5 so as to be normal with respect to a sample 10, contracted by ⅕ times by electrostatic lenses 8, 9, and then irradiated onto the sample 10. Secondary electrons 11 emitted from the sample 10, which have intensities corresponding to the data indicating the pattern on the sample 10, are magnified by electrostatic lenses 9, 8, 12, and 13, and then entered into a detector 14 (a device designated by reference numeral 64 in FIG. 2). The detector 14 generates image signals corresponding to the intensities of the entered second electrons 11, which will be compared to a reference image to detect any defects on the sample 10.

The electrostatic lens 9 and the electrostatic lens 8 together form a symmetric tablet lens unit, while the electrostatic lens 12 and the electrostatic lens 13 also together forms another symmetric tablet lens unit, and so those electrostatic lenses 8, 8, 12 and 13 form a set of distortionless lenses. However, if there is any dirt, for example, on an electrode, the distortion may occur to some extent, and preferably a reference pattern is set on the surface of the sample 11 at regular intervals to measure the distortion so that a parameter for compensating for the distortion may be calculated.

On the other hand, when the sample 11 is such a wafer that includes an oxide film or nitride film selectively formed thereon, only the compensation for the distortion caused by the optical system is not sufficient but it is also required that after the image data having been obtained, a typical point is selected from a pattern edge and the actual data of said point is compared to corresponding ones of the reference image to compensate for the distortion, and then, based on the comparison after this compensation, the defect should be detected.

Further, for the wafer containing a plurality of same dies, a defective portion can be detected by making comparisons among the detected images for respective dies, without any need for using the reference image as stated above. For example, if it is determined that the firstly detected image for one die is not similar to the secondly detected image for the other die, and the thirdly detected image for another die is same or similar to the firstly detected image, then it may be judged that the secondly detected die image does have a defect. If more detailed algorithm for the comparative matching is used, the defective portion defined in the second die image may also be detected.

(Semiconductor Device Manufacturing Method)

Figure 10:
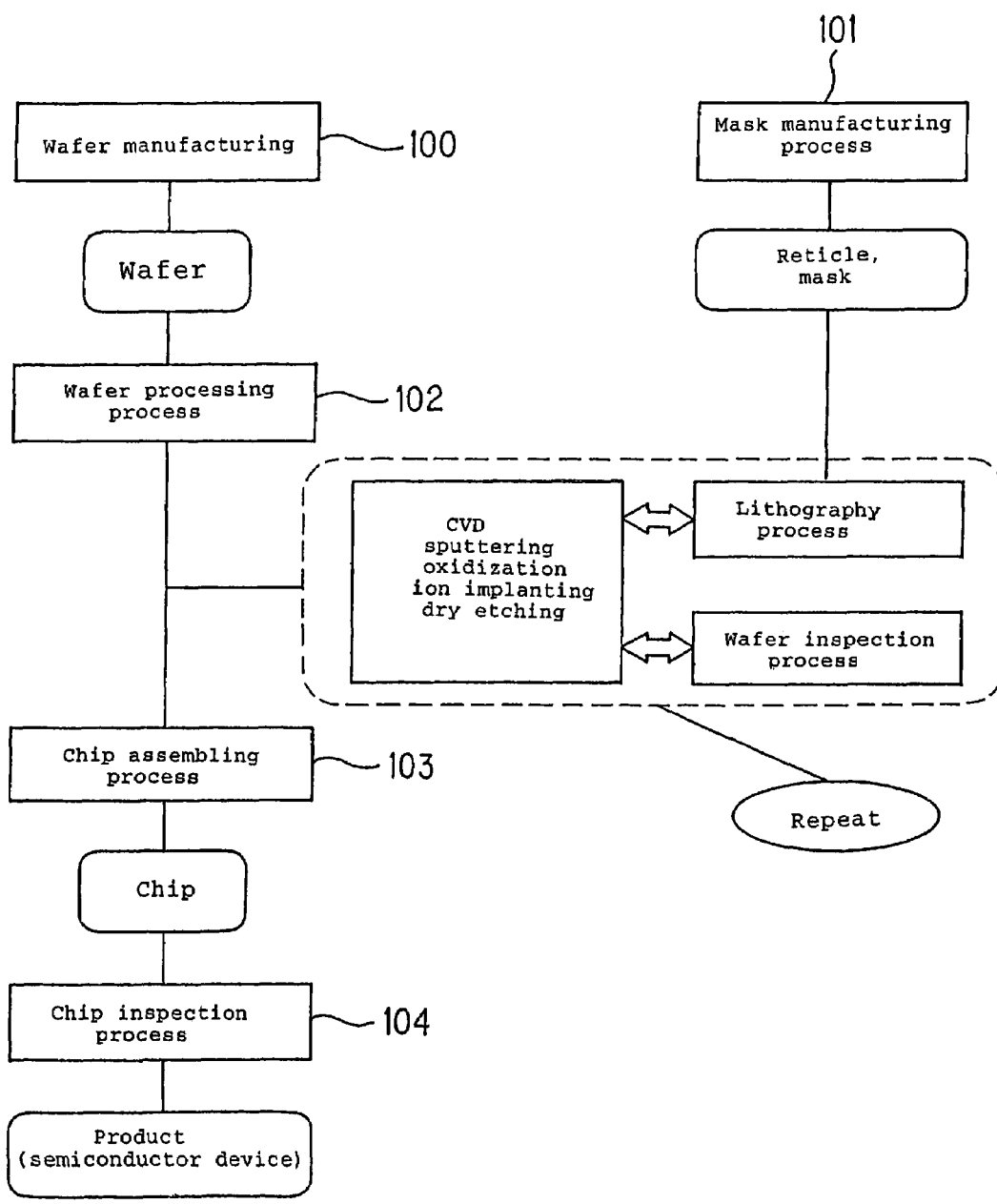
FIG. 10 is a flow chart illustrating an example of a semiconductor device manufacturing method.
Figure 11:
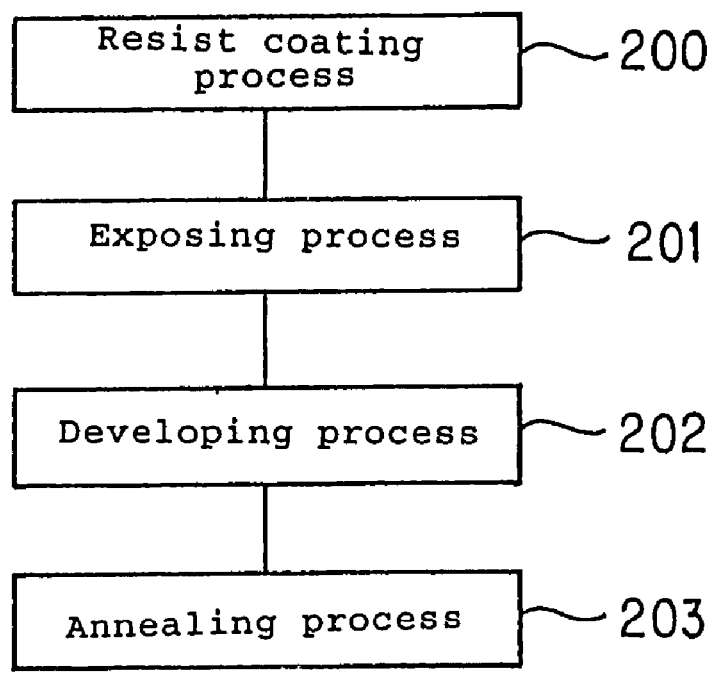
FIG. 11 is a flow chart illustrating a lithography process in the semiconductor device manufacturing method.
Figure 12:
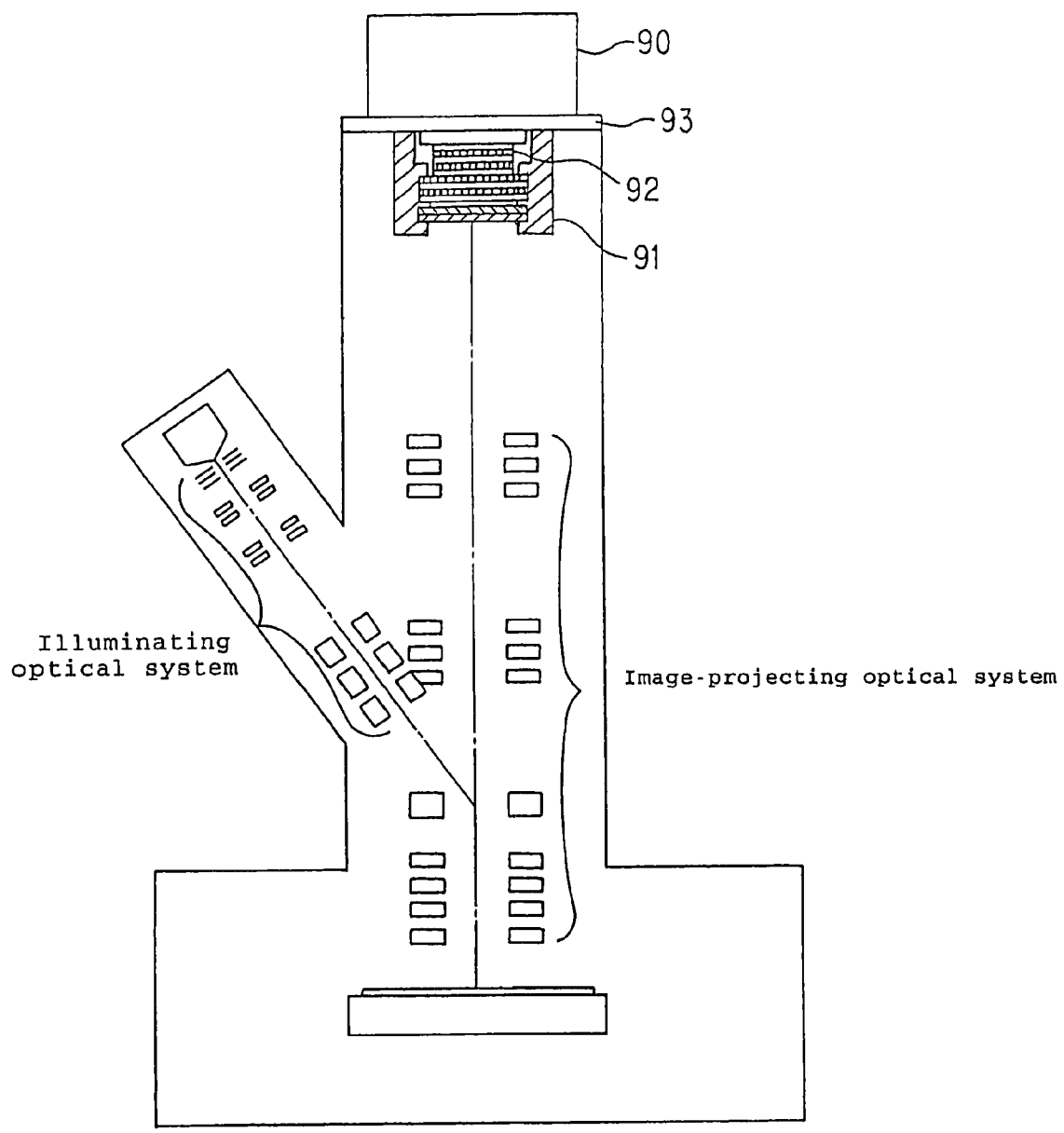
FIG. 12 is a schematic diagram illustrating a surface inspection apparatus according to the prior art.
Figure 13:
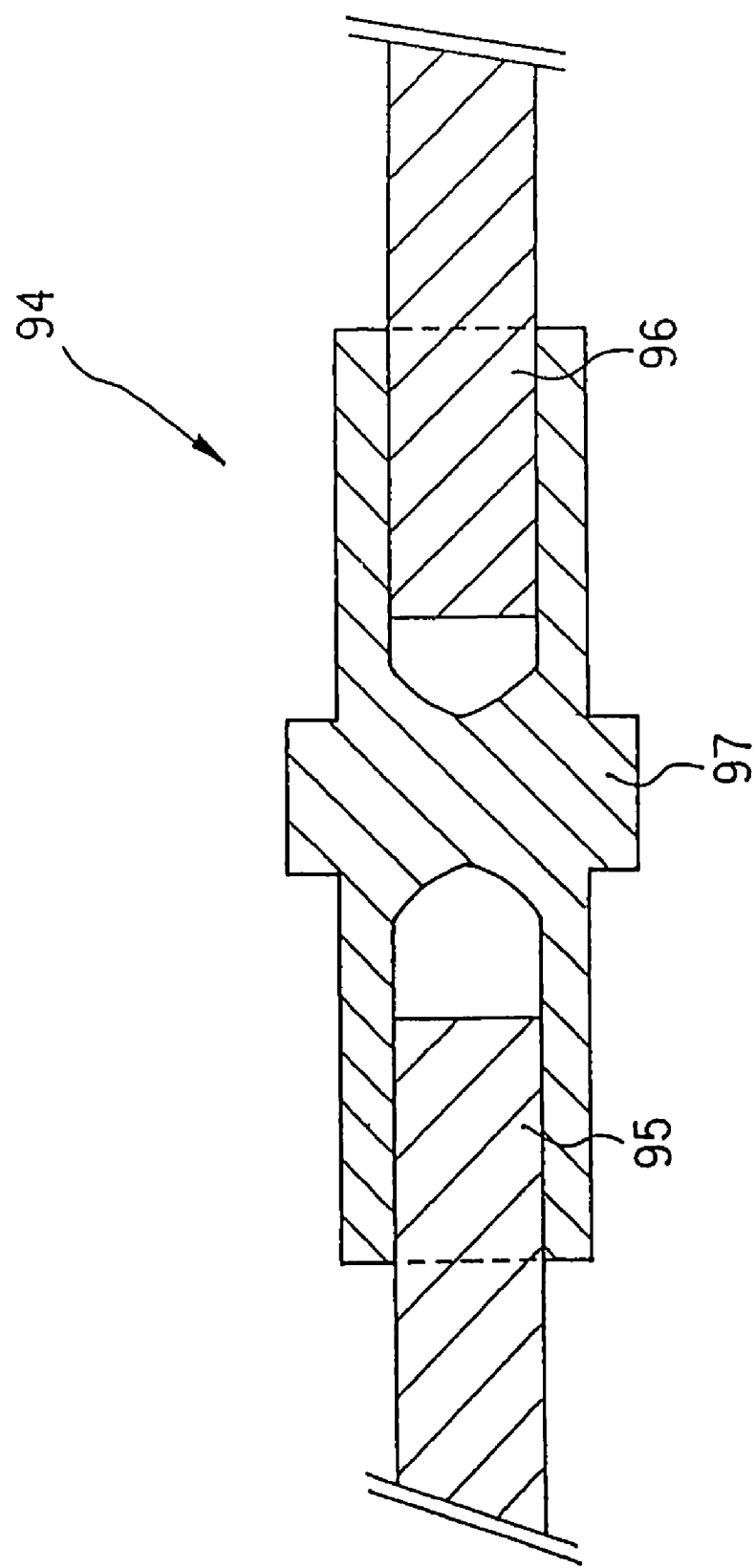
FIG. 13 is a sectional view illustrating a socket and a pin of the feed-through device according to the prior art.
Figure 14:
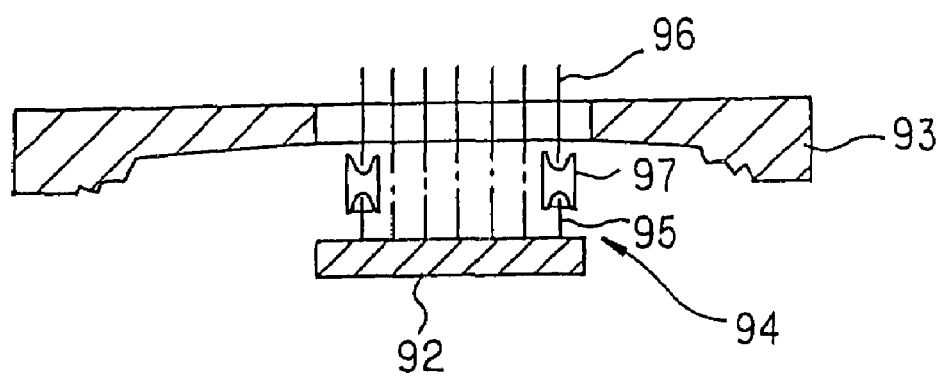
FIG. 14 is a schematic sectional view illustrating a mounting procedure of the socket and the pin of the feed-through device according to said prior art.

Referring to FIG. 10 and FIG. 11, there will now be described an embodiment of a method for manufacturing a semiconductor device by using an electron beam apparatus of image projecting type which is equipped with the feedthrough device as shown in the above embodiments.

FIG. 10 is a flow chart showing an example of the semiconductor device manufacturing method. The manufacturing process of this example includes the following main processes.

(1) A wafer manufacturing process for manufacturing a wafer (or wafer preparing process for preparing a wafer). (Step 100)

(2) A mask manufacturing process for fabricating a mask to be used in the exposure (or a mask preparing process). (Step 101)

(3) A wafer processing process for performing any processing treatments necessary for the wafer. (Step 102)

(4) A chip assembling process for cutting out those chips formed on the wafer one by one to make them operative. (Step 103)

(5) A chip inspection process for inspecting an assembled chip. (Step 104)

It is to be appreciated that each of those processes further comprises several sub-processes.

Among those main processes, the principal process that gives a critical affection to the performance of the semiconductor device is the wafer processing process of (3). In this process, the designed circuit patterns are stacked on the wafer one on another, thus to form many chips, which will function as memories and MPUs. This wafer processing process includes the following sub-processes.

(A) A thin film deposition process for forming a dielectric thin film to be used as an insulation layer and/or a metallic thin film to be formed into a wiring section or an electrode section, or the like (by using the CVD process or the sputtering).

(B) An oxidizing process for oxidizing the formed thin film and/or the wafer substrate.

(C) A lithography process for forming a pattern of the resist by using a mask (reticle) in order to selectively process the thin film layer and/or the wafer substrate.

(D) An etching process for processing the thin film layer and/or the wafer substrate in accordance with the pattern of the resist (by using, for example, the dry etching technology).

(E) An ions/impurities implant and diffusion process.

(F) A resist stripping process.

(G) An inspection process for inspecting the processed wafer.

It should be noted that the wafer processing process must be performed repeatedly as desired depending on the number of layers contained in the wafer, thus to manufacture the device that will be able to operate as designed.

FIG. 11 shows the lithography process included as a core process in said wafer processing process. This lithography process comprises the respective processes as described below.

(a) A resist coating process for coating the wafer having a circuit pattern formed thereon in the preceding stage with the resist. (Step 200)

(b) An exposing process for exposing the resist. (Step 201)

(c) A developing process for developing the exposed resist to obtain the pattern of the resist. (Step 202)

(d) An annealing process for stabilizing the developed pattern. (Step 203)

All of the semiconductor device manufacturing process, the wafer processing process, and the lithography process described above are well known and no additional explanation should be necessary.

When the defect inspection method and the defect inspection apparatus according to the present invention are applied to the wafer inspection process (G) described above, even such a semiconductor device having a minute pattern can be evaluated with high throughput, which enables a 100% inspection and thus improves the yield of the products and prohibits any defective products from being delivered.

What is claimed is:

1. A TDI detecting device having a TDI sensor for detecting an electron image formed through a projection by an image projecting optical system, said device characterized in that:
    an array of pixels in said TDI sensor is adaptively configured based on an optical characteristic of said image projecting optical system.

2. A TDI detecting device in accordance with claim 1, in which said TDI sensor has a number of integration stages which can reduce a field of view of said image projecting optical system to as small as possible so that a maximal acceptable distortion within the field of view may be set larger.

3. A TDI detecting device in accordance with claim 2, in which the number of integration stages has been determined such that a data rate of said sensor may not be reduced but a number of pins in a package may not be increased as much as possible.

4. A TDI detecting device in accordance with claim 3, in which a number of lines is almost equal to the number of integration stages.

5. A TDI detecting device in accordance with either of claim 1 to 4, in which said device has been configured as a package comprising exclusively said TDI sensor.

6. A TDI detecting device in accordance with either of claim 1 to 4, further comprising:
   an image processing means for processing a detection signal from said TDI sensor;
   a flange disposed so as to separate said TDI sensor and said image processing means into different environments respectively; and
   a feed-through means for operatively interconnecting said TDI sensor and said image processing means so as to allow a signal transmission therebetween through said flange.

7. A TDI detecting device in accordance with claim 6, in which said feed-through means comprises:

a second pin connected to said image processing means, which makes a pair with a first pin connected to said TDI sensor; and
   a socket means for connecting said first pin with said second pin, wherein:
   said socket means is equipped with an elastic means for providing an elastic force against a connecting force between said first pin and said second pin.

8. A TDI detecting device in accordance with claim 7, in which said device comprises a plurality of said first pins, said second pins and said socket means, respectively, and said feed-through means defines a plurality of connecting sites.

9. An electron beam apparatus, comprising:
   an electron source for generating a primary electron beam;
   an illuminating optical system for focusing said primary electron beam into an image on a sample;
   an image projecting optical system for image projecting secondary electrons emitted from said sample; and
   a TDI detecting device as defined in claim 7, which is arranged so as to detect an image-projected secondary electron image.

10. A semiconductor device manufacturing method, in which an electron beam apparatus as defined in claim 9 is used to evaluate said sample or a wafer in the course of processing or after at least one of the wafer processing processes having been finished.

* * * * *

UNITED STATES PATENT AND TRADEMARK OFFICE
CERTIFICATE OF CORRECTION

| | | |
|---|---|---|
| PATENT NO. | : 7,521,692 B2 | Page 1 of 1 |
| APPLICATION NO. | : 11/896519 | |
| DATED | : April 21, 2009 | |
| INVENTOR(S) | : Masahiro Hatakeyama et al. | |

It is certified that error appears in the above-identified patent and that said Letters Patent is hereby corrected as shown below:

In Item 62;

Change:

"Related U.S. Application Data

(62) Division of Application No. 10/476,795, filed as application No. PCT/JP02/04655 on May 17, 2002, now Pat. No. 7,285,010."

To be:

--Related U.S. Application Data

(62) Division of Application No. 10/476,795, filed as application No. PCT/JP02/04655 on May 14, 2002, now Pat. No. 7,285,010.--

Signed and Sealed this

First Day of September, 2009

David J. Kappos
*Director of the United States Patent and Trademark Office*